Figure 1:
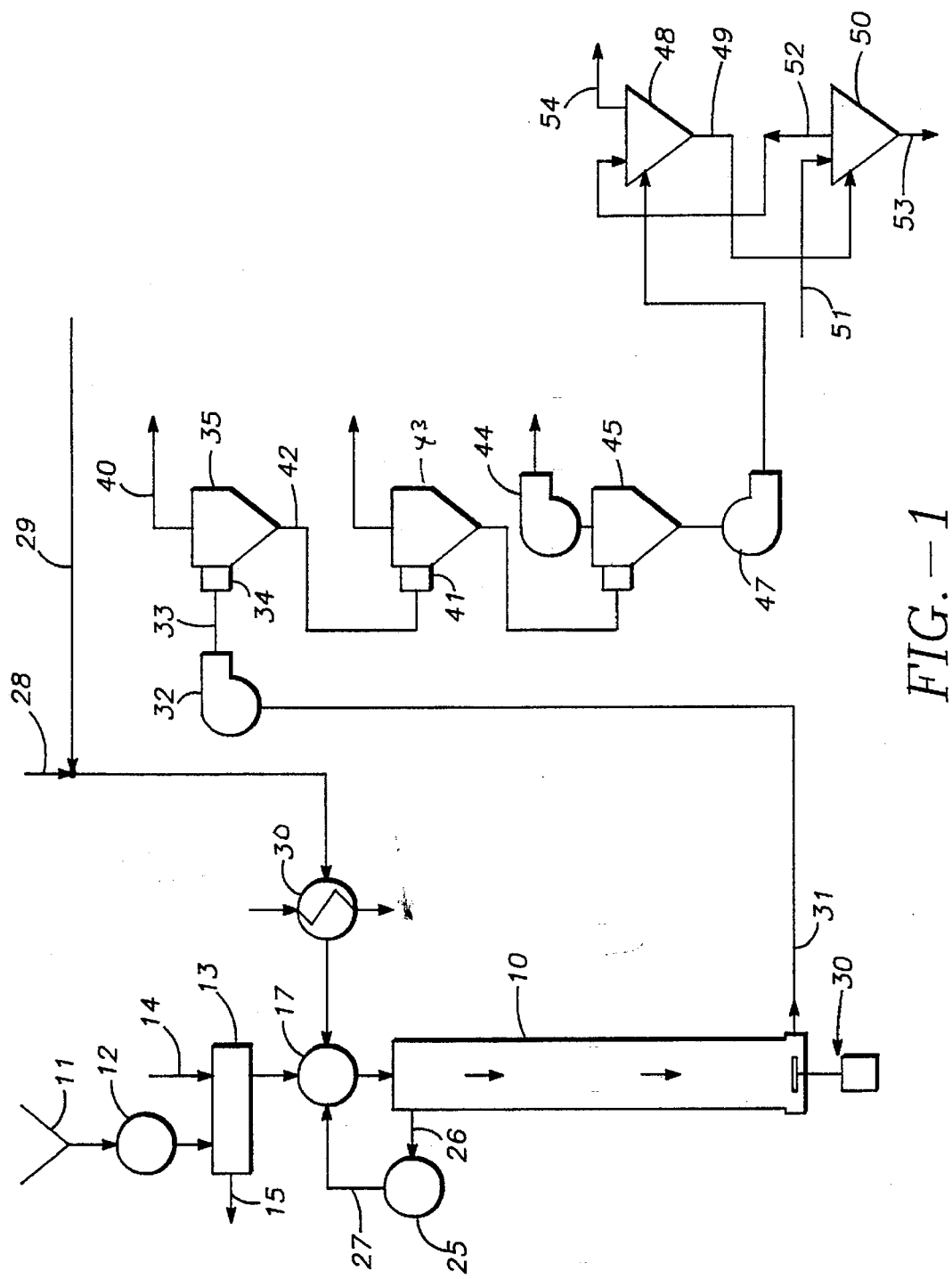

United States Patent [19]

Brink

[11] Patent Number: 5,628,830
[45] Date of Patent: *May 13, 1997

[54] ENZYMATIC HYDROLYSIS OF BIOMASS MATERIAL

[75] Inventor: David L. Brink, Berkeley, Calif.

[73] Assignee: The Regents of the University of California, Oakland, Calif.

[*] Notice: The portion of the term of this patent subsequent to Jun. 22, 2010, has been disclaimed.

[21] Appl. No.: 465,840

[22] Filed: Jun. 6, 1995

Related U.S. Application Data

[63] Continuation-in-part of Ser. No. 254,168, Jun. 6, 1994, Pat. No. 5,536,325, which is a continuation of Ser. No. 73,780, Jun. 8, 1993, Pat. No. 5,366,358, which is a division of Ser. No. 676,836, Mar. 28, 1991, Pat. No. 5,221,357, which is a continuation of Ser. No. 58,814, Jun. 8, 1987, abandoned, which is a continuation-in-part of Ser. No. 681,435, Dec. 13, 1984, abandoned, which is a continuation-in-part of Ser. No. 653,065, Sep. 21, 1984, Pat. No. 4,706,903, which is a continuation-in-part of Ser. No. 324,032, Nov. 23, 1981, Pat. No. 4,384,897, which is a continuation-in-part of Ser. No. 23,328, Mar. 23, 1979, abandoned.

[51] Int. Cl.⁶ .............................. C13K 1/02; C13D 1/00; D21B 1/16; D21C 3/16
[52] U.S. Cl. .............................. 127/36; 127/37; 127/43; 162/25; 162/81
[58] Field of Search .............................. 127/36, 37, 43; 162/25, 81

[56] References Cited

U.S. PATENT DOCUMENTS

| | | | |
|---|---|---|---|
| 2,801,939 | 8/1957 | Hignett et al. | 127/37 |
| 4,281,063 | 7/1981 | Tsao et al. | 435/99 |
| 4,334,026 | 6/1982 | Chynoweth et al. | 127/37 |
| 4,384,897 | 5/1983 | Brink | 127/37 |
| 4,706,903 | 11/1987 | Brink et al. | 241/188 R |
| 5,221,357 | 6/1993 | Brink | 127/37 |
| 5,366,558 | 11/1994 | Brink | 127/43 |
| 5,411,594 | 5/1995 | Brelsford | 127/37 |
| 5,424,417 | 6/1995 | Torget et al. | 127/37 |

OTHER PUBLICATIONS

Wyman et al. (1992) Biomass and Bioenergy 3:301–307. Simultaneous saccharification and fermentation of several lignocellulosic feedstocks to fuel ethanol. Jul. 1992.

*Primary Examiner*—Glenn A. Caldarola
*Assistant Examiner*—Patricia Hailey
*Attorney, Agent, or Firm*—Flehr Hohbach Test Albritton & Herbert, LLP

[57] ABSTRACT

A method of producing sugars and converting the sugars to ethanol in which particulate biomass resulting from hydrolysis of the hemicellulosic content of the biomass is subjected to enzymatic hydrolysis of the cellulosic content to glucose and fermentation of the glucose to ethanol. The particulate biomass resulting from hydrolysis of the hemicellulosic content of the feed stock is reduced to very fine particle size before enzymatic hydrolysis. The hydrolysis of cellulose and the fermentation of the resulting glucose may be carried out separately or they may be carried out simultaneously. The pentoses and hexoses resulting from hydrolysis of the hemicellulose may be subjected to fermentation separately to produce ethanol or they may be fermented simultaneously with the fermentation of the glucose derived from the cellulose.

5 Claims, 1 Drawing Sheet

ENZYMATIC HYDROLYSIS OF BIOMASS MATERIAL

INTRODUCTION

This application is a continuation-in-part of application Ser. No. 08/254,168, filed Jun. 6, 1994, now U.S. Pat. No. 5,536,325, which is a continuation of application Ser. No. 08/073,780, filed Jun. 8, 1993, now U.S. Pat. No. 5,366,358, which is a division of application Ser. No. 07/676,836, filed Mar. 28, 1991, now U.S. Pat. No. 5,221,357, which is a continuation of application Ser. No. 07/058,814, filed Jun. 8, 1987, now abandoned, which is a continuation-in-part of application Ser. No. 06/681,435, filed Dec. 13, 1984, now abandoned, which is a continuation-in-part of application Ser. No. 06/653,065, filed Sep. 21, 1984, now U.S. Pat. No. 4,706,903, which is a continuation-in-part of application Ser. No. 06/324,032, filed Nov. 23, 1981, now U.S. Pat. No. 4,384,897, which is a continuation-in-part of application Ser. No. 06/023,328, filed Mar. 23, 1979, now abandoned.

TECHNICAL FIELD

This invention relates to the production of glucose and ethanol from biomass material such as wood chips, etc.

In my earlier application Ser. No. 08/254,168 and in U.S. Pat. No. 5,366,558 there is described an improved method of producing a glucose solution from biomass in which the raw biomass is first subjected to mild hydrolysis to hydrolyze primarily the hemicellulose content without substantial hydrolysis of the cellulose content, leaving a residue of solid material which contains most of the cellulose and also lignin. This solid biomass is subjected to attrition to reduce it to a finely divided state, e.g. in apparatus as described in U.S. Pat. No. 4,706,903, and the resulting finely divided solids are subjected to acid hydrolysis under more severe conditions to produce a solution of glucose which can then be fermented to produce ethanol.

OBJECTS OF THE INVENTION

It is an object of the present invention to provide an improved method of producing monosaccharides, principally glucose, and ethanol from biomass material.

It is another object of the invention to provide a method of producing glucose, and from it ethanol, from cellulose derived from comminuted solids resulting from first stage hydrolysis as described above and as described in U.S. Pat. No. 5,366,558 and U.S. patent application Ser. No. 08/254,168 filed Jun. 6, 1994 followed by additional attrition of the solids.

SUMMARY OF THE INVENTION

In accordance with the present invention the finely ground solid residue resulting from hydrolysis of the hemicellulose content of biomass material as described in U.S. Pat. No. 5,366,558 and in U.S. patent application Ser. No. 08/254,168 is subjected to enzymatic hydrolysis with a cellulase enzyme or mixture of enzymes to produce an aqueous solution of glucose, and the glucose is fermented to produce ethanol. These two processes i.e., hydrolysis of cellulose to glucose and fermentation of the glucose to ethanol may be carried out simultaneously by using a cellulase enzyme or enzymes to promote hydrolysis of cellulose to glucose followed by microbial agents, for example selected yeast or bacteria, to ferment the glucose and other sugars to ethanol. Alternatively these two steps may be carried out separately and in sequence. Alternatively the second stage hydrolysis may be carried out with acid as described in the aforementioned patent and patent application and thereafter the glucose may be fermented to produce ethanol.

By either of these methods substantially greater yields of ethanol are obtained in shorter times based upon the cellulose content of the biomass material than are obtained by using as a substrate for hydrolysis the solid mass resulting from first stage hydrolysis (i.e., hydrolysis of hemicellulose) but without subjecting the solids resulting from such hydrolysis to attrition to reduce them to a finely divided state.

The starting material of the process from which the aforesaid finely ground solids is derived may be any lignocellulosic material such as biomass as fuel for cogeneration biomass fueled power plants, wood chips used in the manufacture of pulp for papermaking, forest and yard waste such as dead trees, tree stumps, roots, branches and foliage, agricultural waste such as orchard and vineyard trimmings, etc. as described in U.S. Pat. No. 5,366,558. This biomass material, suitably communicated is subjected to first stage hydrolysis (herein referred to as stage 1) using an acid such as sulfuric or nitric acid preferably nitric acid, again as described in U.S. Pat. No. 5,336,538 which is incorporated herein by reference. This stage 1 hydrolysis depolymerizes the hemicellulose content to produce a mixture of sugars including glucose, mannose, xylose, arabinose, and galactose while leaving a solid residue of cellulosic material and ligneous material. This residue is subjected to attrition as, for example, in U.S. Pat. No. 4,706,963 (which is incorporated herein by reference) to a finely divided state. For example, several species of wood may be disintegrated to a fineness as described in Table 1 below.

TABLE 1

| Species | +20 | −20 +40 | −40 +80 | −80 +140 | −180 +200 | −200 |
|---|---|---|---|---|---|---|
| New York hardwood 4 species mixture | 0.0 | 1.0 | 6.4 | 7.1 | 5.6 | 79.6 |
| California manzanita | 0.3 | 1.9 | 8.0 | 6.8 | 83.0 | 9+ |
| White fir | 2.4 | 5.1 | 8.7 | 9.9 | 11.3 | 62.6 |

Referring to the single FIGURE of the drawings, stage 1 hydrolyzer is shown at 10. It is supplied with feed stock by way of hopper 11 and low pressure rotary valve 12, thence to steamer 13 in which steam enters through line 14 and leaves through line 15. The purpose of this steaming is to remove volatiles and air. Then the feed stock enters high pressure rotary valve 17 and is supplied to hydrolyzer 10 where the hemicellulose content is hydrolyzed to sugar. Conditions in the hydrolyzer 10 may be as described in U.S. Pat. No. 5,366,558 as shown in FIG. 2 thereof. A liquid phase is pumped by pump 25 through line 26 and 27 back to valve 17. Makeup acid enters through line 28 and is joined by recycle line 29 and the combined streams are heated by heat exchanger 30 and pass to rotary valve 17 and hydrolyzer 10. At the bottom of hydrolyzer 10 there is a disintegrator 30 which may be constructed and operated like the disintegrator of U.S. Pat. No. 4,706,903 resulting in a slurry of finely divided particles of lignocellulosic material from which the hemicellulose has been removed by hydrolysis. The slurry of hydrolyzate and solids leaves through line 31 and passes to a pump 32 which provides hydrostatic pressure in line 33 which together with rapidly expanding steam, forces the slurry through an orifice 34 with explosive decompression into flash tank 35 at a substantially reduced temperature.

This treatment has the effect of reducing the particle sizes of the solids even more, thus rendering them more susceptible to the catalytic effect of cellulase. By this means a balance can be achieved between disintegration in disintegrator 30 and explosive decompression, thereby minimizing the energy required for the purpose and providing greater activity of the cellulose for enzymatic hydrolysis. Steam and volatile material are removed through line 40 and a more concentrated slurry is removed through line 42. This procedure can be repeated by a slurry pump (not shown) and an orifice 41 leading to flash tank 43. The final stage of flashing is carried out in flash tank 45 from which vapor is pumped by pump 46. Slurry leaves flash tank 45 to pump 47 and thence to separator 48 from which stage hydrolysate leaves through line 54. Solids with adhering aqeueos phase from separator 48 leave through line 49 to separator 50 to which wash water is added through line 51 to carry out one or two displacements of water. Displaced liquid leaves separator 50 through line 52 to separator 48 which is used as a displacement wash. Washed solids leave separator 50 through line 53 for enzymatic hydrolysis and fermentation.

Vapor leaving through line 40 from flash tank 35, through line 43a from flash tank 43 and from flash tank 45 by pump 46 and liquid removed by pump 46 are further processed and liquid is returned, together with make-up water, to line 29. The washed solids leaving separator 50 are processed as follows: 16.18 kg of such solids, sterilized by heat treatment preceding separator 45 are maintained in aseptic condition in subsequent treatment and are subjected to the following processing. They are brought to 38° C. and introduced into a 400 liter fermenter with sterilized deionized water to a solids content of 7% and maintained at 38° C. with agitation to provide a uniform slurry. A 1.0 normal sterilized solution of sodium or ammonium hydroxide is added to adjust the pH and maintain it at 5.0. To this slurry are added a sterilized solution of:

- 0.58 kg of commercial yeast extract and 0.29 kg of peptone (for example, a Difco Corporation product) in 9.76 liters of deionized water.

- Then 2.7 liters of cellulase enzyme are added (for example, Cytolase CL of Genencor International having an activity of 81 standard filter paper units per milliliter.

- Then add 31.5 liters of an inoculum of *Saccharomyces cerevisiae* yeast containing 5.0 gram per liter of dry cell mass prepared under aseptic conditions and diluted with deionized water to bring the fermenter charge to 315 liters.

The contents of the fermenter are maintained at 38° C. with agitation for 96 hours.

The conversion to ethanol of the glycan content of the solids from separator 50 is 89.2% of theoretical yield. Quantitatively the yield of ethanol was 183.3 kg per metric tonne of solids.

Referring to the hydrolysate separated from the solids and leaving through line 54, 144.3 kg, it is processed under aseptic conditions using a well known fermentation procedure. This hydrolysate contains xylose, glucose, mannose, and galactose. In the case of New York hardwood, these monosaccharides are present in the hydrolysis of the amounts of 2.43, 0.31, 0.25 and 0.18%, respectively (w/w %). This hydrolyzate is treated with a slurry of calcium carbonate to produce a pH of 5.0. The resulting slurry is clarified by settling following by centrifugation of the decantate. This sugar solution is brought to pH 6.0 with a solution containing sodium hydroxide and appropriate nutrients and an inoculum of a microbial agent for fermenting both pentoses and hexoses, e.g. *Pichia stipititis* are added. The sugars in this hydrolyzate are fermented in a fermenter at 30° C. with agitation in 65 hours to give a yield of ethanol equivalent to 71.7 kg per metric tonne of feed stock.

The overall yield of ethanol from the two sources is equivalent to 255 kgs per tonne of the New York hardwood feed stock.

The invention has been described above with reference to separate hydrolysis-fermentation of the solids and fermentation of the hydrolysate from stage 1 hydrolysis-disintegrator. These operations may, however, be carried out by subjecting both hydrolysate from stage 1 and the solids from Stage 1 to simultaneous hydrolysis and fermentation without separation of the solid and liquid phases.

Further, the hydrolysis of the cellulose content of the finely divided solids from stage 1 may be carried out by acid hydrolysis as described in U.S. Pat. No. 5,366,558 and then subjecting the resulting hydrolysate to fermentation as described above. However, it is preferred to use enzymatic hydrolysis of the cellulose because the yields are higher. The yields are also augmented by the explosive decompression described above.

I claim:

1. A method of hydrolysis of biomass material containing hemicellulosic, cellulosic and ligneous components which comprises subjecting the biomass material to hydrolysis under conditions to hydrolyze the hemicellulose content without substantial hydrolysis of the cellulosic content, then subjecting residual solid biomass in finely divided particulate form to enzymatic hydrolysis to convert the cellulose to glucose.

2. The method of claim 1 wherein the resulting glucose is fermented to ethanol.

3. The method of claim 2 wherein the enzymatic hydrolysis and the fermentation are carried out simultaneously.

4. The method of any one of claims 1, 2 or 3 wherein the finely divided particulate residual solid biomass is subjected to decompressive explosion through an orifice to further enhance the cellulose to enzymatic hydrolysis to glucose.

5. The method of claim 4, wherein the aqueous phase and particulate solids, after decompressive explosion, are subjected to simultaneous enzymatic hydrolysis and fermentation of both hexose and pentose sugars to yield ethanol.

* * * * *